United States Patent
Pigamo et al.

(10) Patent No.: US 8,309,774 B2
(45) Date of Patent: Nov. 13, 2012

(54) CATALYTIC GAS PHASE FLUORINATION OF 1230XA TO 1234YF

(75) Inventors: Anne Pigamo, Francheville (FR);
Dominique Deur-Bert, Charly (FR);
Laurent Wendlinger, Soucieu en Jarrest (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 13/416,730

(22) Filed: Mar. 9, 2012

(65) Prior Publication Data

US 2012/0172637 A1 Jul. 5, 2012

Related U.S. Application Data

(60) Division of application No. 12/978,172, filed on Dec. 23, 2010, now Pat. No. 8,158,836, which is a continuation-in-part of application No. PCT/IB2009/056054, filed on Dec. 23, 2009.

(51) Int. Cl.
*C07C 21/18* (2006.01)
*C07C 21/04* (2006.01)
*C07C 17/04* (2006.01)
*C07C 17/08* (2006.01)

(52) U.S. Cl. ........ 570/153; 570/124; 570/156; 570/163; 570/165; 570/166; 570/168; 570/169; 570/170

(58) Field of Classification Search .................. 570/124, 570/153, 163, 165, 166, 168, 169, 170
See application file for complete search history.

(56) References Cited

U.S. PATENT DOCUMENTS

| | | | |
|---|---|---|---|
| 4,902,838 A | 2/1990 | Manzer et al. | |
| 5,616,819 A * | 4/1997 | Boyce et al. | 570/167 |
| 5,714,651 A | 2/1998 | Elsheikh et al. | |
| 5,731,481 A | 3/1998 | Cheminal et al. | |
| 5,895,825 A * | 4/1999 | Elsheikh et al. | 570/167 |
| 7,485,598 B2 | 2/2009 | Elsheikh et al. | |
| 8,071,825 B2 * | 12/2011 | Johnson et al. | 570/155 |
| 8,076,521 B2 * | 12/2011 | Elsheikh et al. | 570/160 |
| 2009/0030244 A1 * | 1/2009 | Merkel et al. | 570/135 |
| 2009/0030245 A1 | 1/2009 | Ma et al. | |
| 2009/0224207 A1 * | 9/2009 | Pham et al. | 252/372 |
| 2009/0240090 A1 * | 9/2009 | Merkel et al. | 570/160 |
| 2010/0130599 A1 * | 5/2010 | Coty et al. | 514/457 |
| 2010/0185030 A1 * | 7/2010 | Elsheikh et al. | 570/160 |

(Continued)

FOREIGN PATENT DOCUMENTS

EP 0 939 071 A1 * 9/1999

(Continued)

OTHER PUBLICATIONS

International Search Report for International Application No. PCT/IB2009/056054, mailed Oct. 22, 2010.

(Continued)

*Primary Examiner* — Joseph D Anthony
(74) *Attorney, Agent, or Firm* — Hunton & Williams, LLP

(57) ABSTRACT

The invention is directed to a process for preparing 2,2,2,3-tetrafluoropropene (1234yf), comprising:
(i) contacting 1,1,2,3-tetrachloropropene (1230xa) with hydrogen fluoride HF in gas phase in the presence of a fluorination catalyst under conditions sufficient to produce a reaction mixture;
(ii) separating the reaction mixture into a first stream comprising HCl, 2,2,2,3-tetrafluoropropene (1234yf) and a second stream comprising HF, 2-chloro-3,3,3-trifluoro-1-propene (1233xf) and 1,1,1,2,2-pentafluoropropane (245cb);
(iii) recycling at least a part of the second stream at least in part back to step (i).

7 Claims, 2 Drawing Sheets

U.S. PATENT DOCUMENTS

| | | | |
|---|---|---|---|
| 2010/0331583 A1* | 12/2010 | Johnson et al. | 570/156 |
| 2011/0105809 A1* | 5/2011 | Devic et al. | 570/179 |
| 2011/0160497 A1* | 6/2011 | Deur-Bert et al. | 570/153 |
| 2011/0160499 A1* | 6/2011 | Wendlinger et al. | 570/158 |
| 2011/0313215 A2* | 12/2011 | Wendlinger et al. | 570/158 |

FOREIGN PATENT DOCUMENTS

| | | |
|---|---|---|
| WO | WO 2007/079431 A2 * | 7/2007 |
| WO | WO 2008/002500 A1 * | 1/2008 |
| WO | WO 2008/040969 A2 * | 4/2008 |
| WO | WO 2008/054781 A1 * | 5/2008 |
| WO | WO 2009/002084 A1 * | 12/2008 |
| WO | WO 2009/003084 | 12/2008 |
| WO | WO 2009/015317 A1 * | 1/2009 |
| WO | WO 2009/118628 A1 * | 10/2009 |
| WO | WO 2009/158321 | 12/2009 |

OTHER PUBLICATIONS

Written Opinion for International Application No. PCT/IB2009/056054, mailed Oct. 22, 2010.

* cited by examiner

CATALYTIC GAS PHASE FLUORINATION OF 1230XA TO 1234YF

CROSS-REFERENCE TO RELATED APPLICATIONS

This application is a divisional of U.S. application Ser. No. 12/978,172, filed Dec. 23, 2010, now U.S. Pat. No. 8,358,836, which is a continuation in part of International Application No. PCT/IB2009/056054 filed on Dec. 23, 2009, both of which are incorporated by reference herein in their entireties.

FIELD OF THE INVENTION

The present invention relates to the gas phase catalyzed fluorination of 1,1,2,3-tetrachloropropene (1230xa) to produce 2,2,2,3-tetrafluoropropene (1234yf). More particularly, the present invention relates to processes wherein 1230xa; optionally containing a low level of polymerization inhibitor, is contacted with hydrogen fluoride (HF) in a gas phase reaction, in the presence of a fluorination catalyst to produce 1234yf. The desired product, 1234yf is known to have utility as a foam blowing agent, refrigerant, aerosol propellant, heat transfer media, fire extinguisher, etc. Furthermore, 1234yf is known to have zero Ozone Depletion Potential (ODP) and very low Global Warming Potential (GWP) of much less than 150.

BACKGROUND OF THE INVENTION

The Montreal Protocol for the protection of the ozone layer mandated the phase out of the use of chlorofluorocarbons (CFCs). Materials more "friendly" to the ozone layer, such as hydrofluorocarbons (HFCs) e.g. HFC-134a replaced chlorofluorocarbons. The latter compounds have proven to be green house gases, causing global warming and were regulated by the Kyoto Protocol on Climate Change. With the continued concern over global climate change there is an increasing need to develop technologies to replace those with high ozone depletion potential (ODP) and high global warming potential (GWP). Though hydrofluorocarbons (HFCs), being non-ozone depleting compounds, have been identified as alternatives to chlorofluorocarbons (CFCs) and hydrochloro-fluorocarbons (HCFCs) as solvents, cleaning agents and heat transfer fluids, they still tend to have significant GWP. Hydrofluoroolefins (HFO) have been identified as potential alternatives with zero ODP and low GWP.

Hence, numerous documents have provided such HFOs. Methods of preparing hydrofluoroalkenes are known. For example, WO2007/079431 discloses processes for the production of fluorinated olefins, including hydrofluoropropenes. The processes which are broadly described as a single reaction or two or more reactions involve fluorination of compound of the formula $C(X)_mCCl(Y)_nC(X)_m$ to at least one compound of formula $CF_3CF=CHZ$, where each X, Y and Z is independently H, F, Cl, I or Br and each m is independently 1, 2 or 3 and n is 0 or 1. 1234yf is prepared by fluorinating 1233xf into 1,1,1,2-tetrafluoro-2-chloropropane (HFC244bb), followed by dehydrochlorination. 1233xf is prepared by trifluorination of the corresponding chlorinated precursor ($CCl_2=CClCH_2Cl$).

EP-A-939071 discloses, among many possibilities, gas-phase fluorination of an halogenated propene (including in the list 1230xa) into a fluorinated propene (including in the list 1234yf).

WO2008/054781 discloses a variety of processes for producing a variety of fluoropropanes and halofluoropropenes by reacting halopropanes or halopropenes with HF optionally in the presence of a catalyst. It discloses a process for making 1234yf by reacting 2,3-dichloro-1,1,1-trifluoropropane (243 db) in the presence of HF, on a catalyst, especially Cr/Co 98/2. Reaction products comprise 1234yf and 2-chloro-3,3,3-trifluoro-1-propene (1233xf), the latter being the main product; other products being 1-chloro-3,3,3-trifluoro-1-propene (1233zd) as well as 245cb and 1234ze which are also formed.

WO2008/002500 discloses a process for making a mixture of 2,3,3,3-tetrafluoro-1-propene (HFO 1234yf) and 1,3,3,3-tetrafluoro-1-propene (HFO 1234ze) by catalytic conversion of 1,1,1,2,3-pentafluoropropane (HFC 245eb) on a dehydrofluorination catalyst.

WO2008/040969 discloses a process comprising dehydrochlorination of 243 db into 1233 (xf as well as zd), followed by a reaction involving formation of 1,1,1,2-tetrafluoro-2-chloropropane (244bb) and later formation of the desired 2,3,3,3-tetrafluoro-1-propene through dehydrochlorination. Example 1 of said document discloses a gas phase reaction at atmospheric pressure of 243 db with HF on a Zn/chromia catalyst, whereby 1234yf and 1233xf are formed, together with a small amount of 245cb. Example 2 of said document discloses a gas phase reaction at atmospheric pressure of 245cb in presence of HF on the same catalyst (contact time 5 sec) whereby 1234yf is formed.

WO2009/015317 discloses the reaction of a chlorinated compound which can be 1,1,2,3-tetrachloro-1-propene (1230xa), 1,1,1,2,3-pentachloropropane (240 db) or 2,3,3,3-tetrachloro-1-propene (1230xf) with HF, in gas phase, on a catalyst and in the presence of at least one stabilizer. This process allows obtaining 2-Chloro-3,3,3-trifluoro-1-propene (1233xf).

US2009/0240090 discloses a process for making 2,3,3,3-tetrafluoro-1-propene (1234yf) starting from a compound of formula (I) $CX_2=CClCH_2X$, or formula (II) $CX_3CCl=CH_2$ or formula (III) $CX_3CHClCH_2X$ with X=F, Cl, Br, I. The process comprises three steps, which can be followed by purification. The process includes recycling steps allowing higher conversions and yields.

SUMMARY OF THE INVENTION

The invention is thus directed to a process for preparing 2,2,2,3-tetrafluoropropene (1234yf), comprising:
(i) contacting 1,1,2,3-tetrachloropropene (1230xa) with hydrogen fluoride HF in gas phase in the presence of a fluorination catalyst under conditions sufficient to produce a reaction mixture;
(ii) separating the reaction mixture into a first stream comprising HCl, 2,2,2,3-tetrafluoropropene (1234yf) and a second stream comprising HF, 2-chloro-3,3,3-trifluoro-1-propene (1233xf) and 1,1,1,2,2-pentafluoropropane (245cb);
(iii) recycling at least a part of the second stream at least in part back to step (i).

Embodiments are the following:
the reaction mixture obtained at step (i) comprises 2,2,2,3-tetrafluoropropene (1234yf) and 1,1,1,2,2-pentafluoropropane (245cb) in a molar ratio of 1:5 to 3:1, preferably 1:4 to 2:1.
the reaction mixture obtained at step (i) comprises 2,2,2,3-tetrafluoropropene (1234yf), 1,1,1,2,2-pentafluoropropane (245cb) and 1,1,1,2-tetrafluoro-2-chloropropane (244bb) such that the molar ratio of. 245cb to 244bb is from 1:1 to 70:1, preferably from 1.5:1 to 65:1.

step (i) is carried out with a molar ratio HF:1230xa from 3:1 to 150:1, preferably 4:1 to 70:1, more preferably 5:1 to 50:1.

step (i) is carried out at a pressure from 3 to 20 bars, preferably 5 to 15 bars, more preferably 7 to 10 bars.

step (i) is carried out at a temperature of from 200 to 450° C., preferably from 300 to 430° C., more preferably from 320 to 420° C.

step (i) is carried out with a contact time from 6 to 100 sec, preferably from 10 to 80 sec, more preferably from 15 to 50 sec.

step (i) is carried out in the presence of $O_2$ and/or $Cl_2$.

the ratio of $O_2$ and/or $Cl_2$ with respect to 1,1,2,3-tetrachloropropene (1230xa) is 0.05 to 15 mole %, preferably 0.5 to 10 mole %.

step (ii) is a distillation step.

the first stream is further separated into HCl and 2,2,2,3-tetrafluoropropene (1234yf), preferably in a distillation step.

step (i) is carried out in the presence of a polymerization inhibitor, preferably chosen from the group consisting of p-methoxyphenol, t-amylphenol, limonene, d,l-limonene, quinones, hydroquinones, epoxides, amines and mixtures thereof.

step (i) is carried out in the presence of a catalyst comprising Ni—Cr, preferably supported.

said catalyst is supported on a support selected from fluorinated alumina, fluorinated chromia, fluorinated activated carbon or graphite carbon.

step (i) is carried out in the presence of a catalyst which is a chromium catalyst, supported or unsupported, preferably unsupported.

said catalyst further comprises a co-catalyst selected from Ni, Co, Zn, Mn, Mg or mixtures thereof, preferably nickel and magnesium, and wherein said co-catalyst is preferably present in an amount from about 1-10 wt % of said fluorination catalyst.

said fluorination catalyst is activated with a fluorine-containing compound, preferably hydrogen fluoride, and preferably at a pressure above 10 bars.

the process is continuous.

The invention is also directed to a composition containing 2,2,2,3-tetrafluoropropene (1234yf), 1,1,1,2,2-pentafluoropropane (245cb) and 1,1,1,2-tetrafluoro-2-chloropropane (244bb) such that the molar ratio of 245cb to 244bb is from 1:1 to 70:1, and the molar ratio of 1234yf:245cb is from 1:5 to 3:1.

Embodiments are the following:

the molar ratio of 245cb to 244bb is from 1.5:1 to 65:1, and the molar ratio of 1234yf:245cb is from 1:4 to 2:1.

the composition further contains 2-chloro-3,3,3-trifluoro-1-propen (1233xf) and optionally HF and HCl.

BRIEF DISCLOSURE OF THE DRAWINGS

DETAILED DESCRIPTION OF EMBODIMENTS OF THE INVENTION

Figure 1:
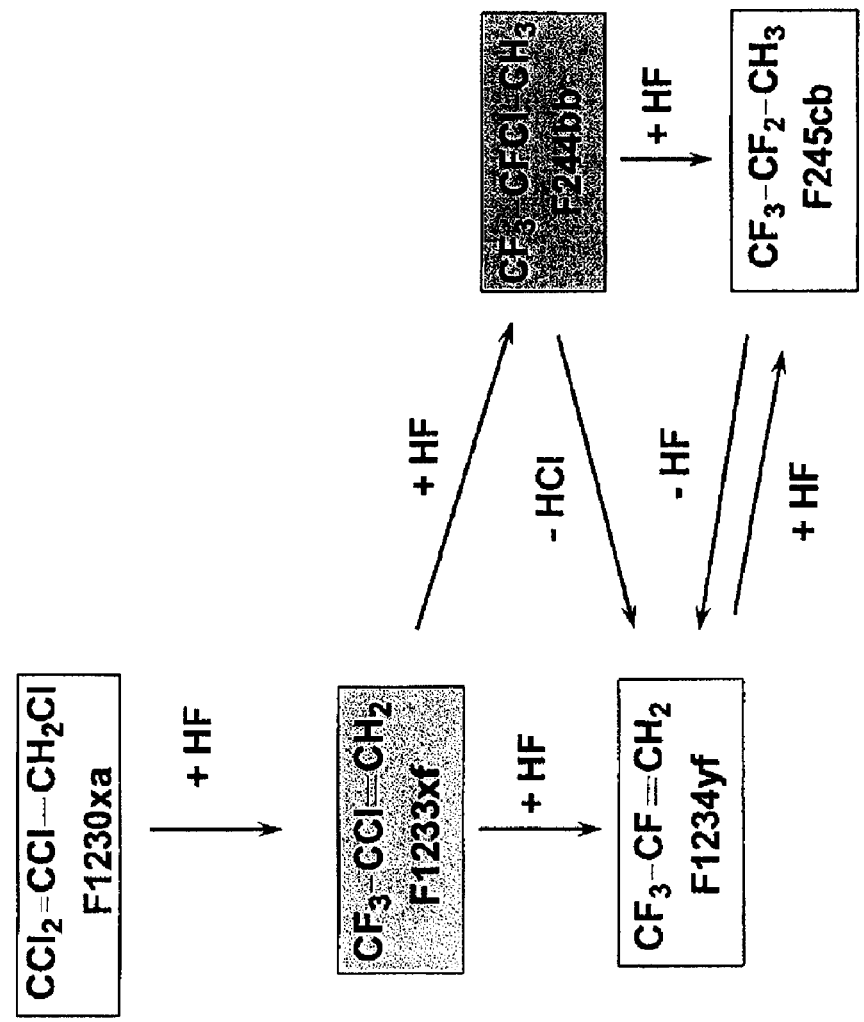
FIG. 1 is a scheme representing the possible reactions involved in the present invention.

FIG. 1 provides a scheme of potential reactions involved in the instant process. The first reaction is the hydrofluorination of 1230xa into 1233xf. Then 1233xf undergoes a series of possible reactions. Reaction with HF can lead directly to 1234yf or through an addition reaction to a saturated compound 244bb. This saturated compound can be dehydrochlorinated to give 1234yf. 244bb can also, upon fluorination with HF, give 245cb. 1234yf and 245cb form an equilibrium; the invention is based on this finding. Any 245cb formed can be recycled to the first reaction zone, whereby the equilibrium is displaced (1234yf being thus prevented from further conversion into 245cb). The 245cb flowrate in the recycling loop (either at the exit of the gas-phase reactor or in the second stream back exiting the distillation column and back to the gas-phase reactor) is thus substantially constant. No 245cb build up will thus take place in the recycling loop. In this instance, 1230xa fed into the reactor converts only into 1233xf and 1234yf since 245cb is already present in the recycling loop.

Figure 2:
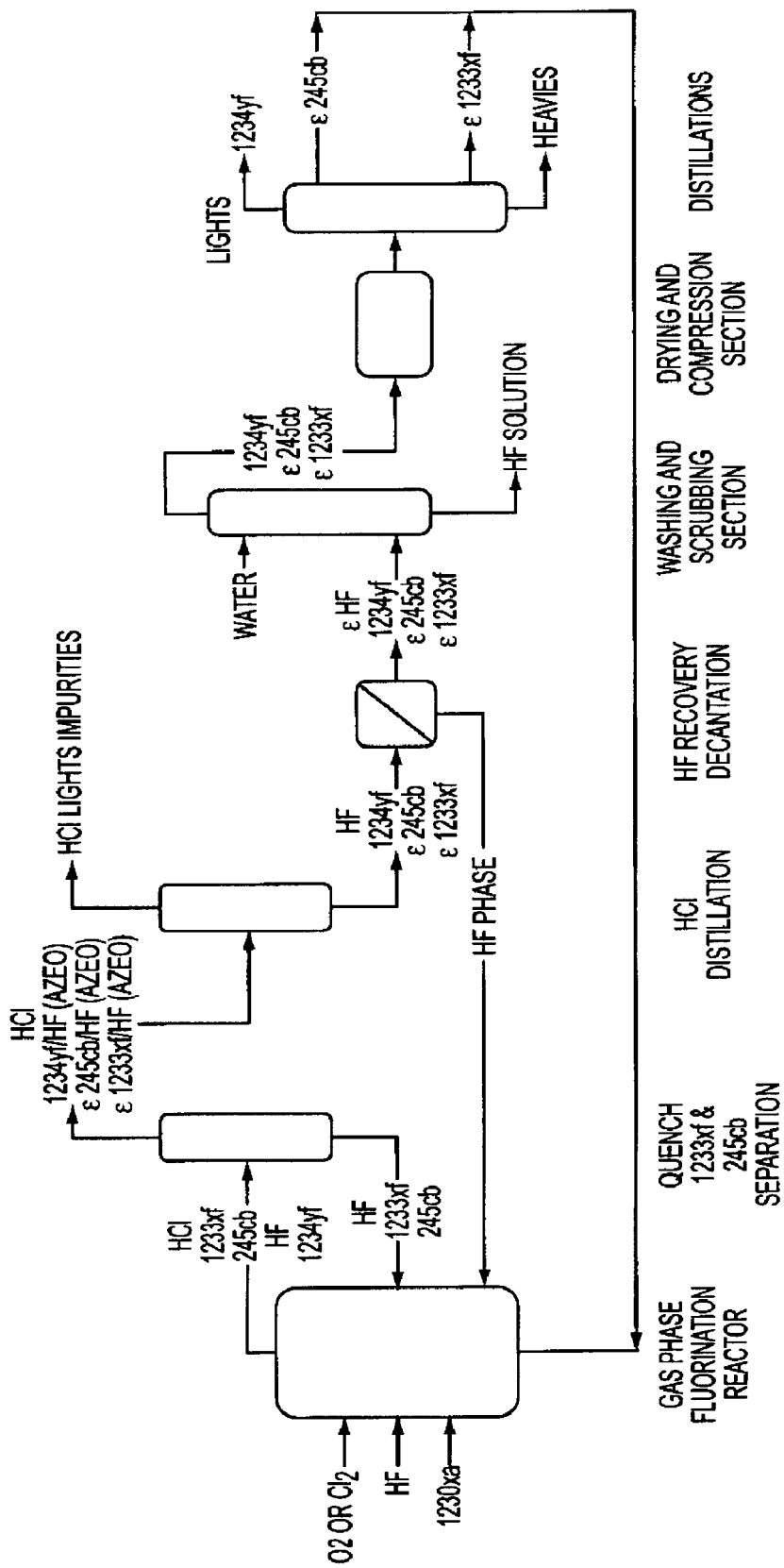
FIG. 2 is a scheme representing the process carried out in the invention.

FIG. 2 represents the process carried out in the invention. The gas-phase reactor is fed with 1230xa and HF. The reaction mixture exiting the reactor comprises HCl, 1233xf, unreacted HF, 1234yf, 245cb and a minor amount of 244bb. This reaction stream is separated by distillation into a first stream (light products) comprising HCl, 1234yf (possibly with a small amount of HF thereby forming an azeotropic mixture) and minor amounts of 245cb and 1233xf. A second, heavier, stream is obtained at the bottom of the distillation column, and comprises HF, 1233xf, 245cb and minor amounts of 244bb. The lighter fraction containing HCl, 1234yf (with HF) and minor amounts other products is again distillated. The top flow comprises HCl, while the bottom flow comprises 1234yf and HF, which can again be separated using appropriate known methods. Among known methods is the decantation, which produces an HF rich flow which can be recycled to the gas-phase reactor. This decreases the fluorine content downstream in the process, generating less side-products (e.g. $CaF_2$ which must be discarded). The streams exiting the decantation are treated according to known methods, including washing and scrubbing and distillations.

The applicant has found that the stream exiting the gas-phase reactor has a specific composition, due to the recycling of 245cb. Hence, the invention provides also a composition containing 2,2,2,3-tetrafluoropropene (1234yf), 1,1,1,2,2-pentafluoropropane (245cb) and 1,1,1,2-tetrafluoro-2-chloropropane (244bb) such that the molar ratio of 245cb to 244bb is from 1:1 to 70:1, and the molar ratio of 1234yf:245cb is from 1:5 to 3:1; preferably the molar ratio of 245cb to 244bb is from 1.5:1 to 65:1, and the molar ratio of 1234yf:245cb is from 1:4 to 2:1. The composition may also comprise 1233xf, and optionally other compounds such as unreacted HF and HCl.

The gas phase reaction is carried out in the presence of a fluorination catalyst. The reaction is carried out in a single gas-phase reactor.

The level of the conversion and selectivity of the desired product can vary according to the processing conditions. The catalyst can be present in any suitable form, such as fixed or fluidized bed, preferably in a fixed bed. The direction of flow may be downward or upward.

This catalyst is for example a catalyst based on a metal including a transition metal oxide or a derivative or halide or oxyhalide such a metal. Catalysts are e.g. $FeCl_3$, chromium oxyfluoride, chromium oxides (that can optionally be subject to fluorination treatments), chromium fluorides, and mixtures thereof. Other possible catalysts are the catalysts supported on carbon catalysts based on antimony, catalysts based on aluminum (as $AlF_3$ and $Al_2O_3$ and oxyfluoride of alumina and aluminum fluoride). Generally speaking, catalysts that can be used are chromium oxyfluoride, aluminium fluorure and oxyfluoride, and supported or unsupported catalyst containing a metal such as Cr, Ni, Zn, Ti, V, Zr, Mo, Ge, Sn, Pb, Mg. Reference can also be made to the disclosures of WO-A-2007/079431, at page 7, lines 1-5 and 28-32, EP-A-939071, at paragraph [0022], WO2008/054781 at page 9 line 22 to page 10 line 34, WO2008/040969 in claim 1, all incorporated herein by reference.

Prior to its use, the catalyst is subjected to activation with HF at high pressure, typically above about 10 bars (typically at a pressure above the pressure used in the gas-phase process), as described in U.S. Pat. No. 7,485,598, incorporated herein by reference.

A preferred embodiment uses a particular catalyst, which is a mixed catalyst, containing both chromium and nickel. The molar ratio Cr:Ni, with respect to the metallic element is generally between 0.5 and 5, for example between 0.7 and 2, including close to 1. The catalyst may contain in weight from 0.5 to 20% chromium and 0.5 to 20% nickel, preferably between 2 and 10% of each metal.

The metal may be present in metallic form or as derivatives, including oxide, halide or oxyhalide. These derivatives, including halide and halide oxides, are obtained by activation of the catalytic metal. Although the activation of the metal is not necessary, it is preferred.

The support is preferably made from aluminum. There are several possible carriers such as alumina, activated alumina or aluminum derivatives. These derivatives include aluminum halides and halide oxides of aluminum, for example described in U.S. Pat. No. 4,902,838, or obtained by the activation process described below.

The catalyst may include chromium and nickel in a non-activated or activated form, on a support that has been subjected to activation or not.

Reference can be made to WO2009/118628, and especially to the disclosure of the catalyst from page 4, line 30 to page 7, line 16, which is incorporated herein by reference.

According to another embodiment, the process uses a high surface area Cr based catalyst which is preferably unsupported. The catalyst can optionally contain a low level of one or more co-catalyst such as Co, Zn, Mn, Mg and Ni salt. A preferred co-catalyst is nickel or magnesium. Another preferred co-catalyst is Zn.

The preferred unsupported chromium catalyst can optionally contain low levels of one or more co-catalysts selected from cobalt, nickel, zinc, manganese or magnesium, prepared by processes known in the art, such as impregnation, mixed powder and the like. The catalyst can be supported or unsupported. For supported catalyst, the catalyst support can be selected from materials known in the art to be compatible with HF at higher temperature and pressure. For example, fluorinated alumina, prefluorinated activated carbon, graphite or fluorinated graphite are suitable catalyst supports. A preferred chromium catalyst is a high surface area unsupported chromium oxide catalyst. The catalyst is activated before use. The catalyst activation typically comprises a high pressure, above 10 bars, procedure wherein the catalyst bed is heated to about 370-380° C., preferably with a continuous flow of nitrogen, after which a mixture of approximately equal volumes of HF and air or nitrogen (preferably nitrogen) are fed over the catalyst bed. The catalyst activation process can be as described in U.S. Pat. No. 7,485,598, incorporated herein by reference. Other fluorinated organic compounds such as $CHF_2Cl$, $CHF_3$, $CF_3CH_2F$, $CF_3CH_2Cl$ and the like can be used for activation. Typically the high pressure catalyst activation procedure takes about 18 hours.

The resulted high-pressure activated catalyst has a high surface area, such as from about 20 to about 250 square meters per gram. The fluorine content typically varies between about 20 to 25 wt %. The pore volume has an average value between 0.1 to 0.4 $m^3/g$. Crushing strength is typically between about 8 to 15 kg/g. Percent attrition is typically on average between 1 to 5 wt %. $Cr^{(VI)}$ level is typically in the range of 100 to 300 ppm.

The level of the co-catalyst, when present, can be varied between 1 to 10 wt %, preferable between 1 to 5 wt %. Co-catalyst can be added to the catalyst by processes known in the art such as adsorption from an aqueous or organic solution, followed by solvent evaporation. The preferred catalyst in this embodiment is pure chromium oxide with nickel or zinc as a co-catalyst. Alternatively the co-catalyst can be physically mixed with the catalyst via grinding to produce an intimate mixture. An alternative catalyst is a mixed chromium/nickel catalyst supported on fluorinated alumina. U.S. Pat. No. 5,731,481, incorporated herein by reference, discloses a method of preparation of this alternative catalyst which would be activated as described hereinabove.

For example, a catalyst which can be used in the invention can be prepared as follows. A $Cr_2O_3$ catalyst was activated at 16 bars and 350° C. using HF and nitrogen gas. The chemical and physical properties of the resulting catalyst are shown in the table below.

| | |
|---|---|
| % F Content wt % | 22.2 |
| Surface Area $m^2/g^1$ | 43.9 |
| Pore Volume $m^3/g^2$ | 0.19 |
| Crush Strength $kg/g^3$ | 10.6 |
| $Cr^{+VI}$ content ppm | 201 |
| % Attrition[4] | 3.9 |

[1]Surface area was determined by the BET surface area by Micrometrics ASAP 2400
[2]Pore volume was evaluated using xylene porosity measurement.
[3]Crush strength was evaluated by applying a specified rate of compression, until the integrity of the catalyst is compromised.
[4]Percent Attrition was evaluated by using ASTM D-4058-92 Standard test method for attrition.

The process of the present invention is preferably run continuously.

The 1230xa fluorination process involves contacting 1230xa with HF in the reaction zone in a gas phase, under conditions sufficient to convert the 1230xa to fluorination products comprising 1233xf, 1234yf and 245cb. Such conditions are given below. In addition, other co-produced under-fluorinated intermediates such as 1233xf (and 244bb which may be present in minor amounts) which are produced as part of the fluorination reaction are also recycled to the reactor. The recycle stream contains the heavy fraction of the reaction stream which has been separated in the distillation step, and especially the equilibrated 245cb.

Typically, step (i) is carried out with a molar ratio HF:1230xa from 3:1 to 150:1, preferably 4:1 to 70:1, more preferably 5:1 to 50:1.

Typically, step (i) is carried out at a pressure from 3 to 20 bars, preferably 5 to 15 bars, more preferably 7 to 10 bars.

Typically, step (i) is carried out at a temperature of from 200 to 450° C., preferably from 300 to 430° C., more preferably from 320 to 420° C. The temperature of the bed can be substantially uniform in the reactor or can be adjusted along the path of the stream, decreasing or increasing along the direction of flow.

Contact times (catalyst volume divided by the total flow rate of reactants and co-feeds, adjusted to the operating pressure and temperature) are typically from 6 to 100 sec, preferably from 10 to 80 sec, more preferably from 15 to 50 sec.

An oxygen co-feed or chlorine co-feed can be used to extend the catalyst lifetime, typically in an amount of from 0.05 to 15 mole %, preferably 0.5 to 10 mole % of oxygen or chlorine per 1230xa. The oxygen can be introduced as an oxygen-containing gas such as air, pure oxygen, or an oxygen/nitrogen mixture. Chlorine can be introduced as a chlorine-containing gas such as pure chlorine, or a chlorine/nitrogen mixture.

A polymerization inhibitor can be used to extend the catalyst life, typically in a concentration of from about 50-1000 ppm, more preferably between 100-500 ppm. The polymerization inhibitor can be p-methoxyphenol, t-amylphenol, limonene, d,l-limonene, quinones, hydroquinones, epoxides, amines and mixtures thereof. The preferred polymerization inhibitor is p-methoxyphenol or t-amylphenol. The co-feeding of a low level of a polymerization inhibitor can control such polymerization of chloroolefins and extend the life of the catalyst as described in U.S. Pat. No. 5,714,651, incorporated herein by reference.

Conversion of 1230xa is typically higher than 90%, preferably higher than 95% and more preferably higher than 97%.

The reactants can be fed to the reactor at the same location, at different locations, or using staged feeding at staged locations along the reactor. A preferred feeding system is to blow the gaseous reactants at the bottom of the reactor. Recycling can be done at the entry of the reactor or at an intermediate stage of the reactor; preferably at the entry of the reactor.

In another embodiment, the reaction stream exiting the gas-phase reactor can be recycled in part to the reactor, before it is subjected to the separation into a first, light, stream and a second, heavy stream. The recycling ratio can be as high as 0.7. This recycling allows dilution of 1230xa which is very reactive and avoids polymerisation.

Reactions are implemented in a dedicated reactor for reactions involving halogens. Such reactors are known to those skilled in the art and can include linings based eg Hastelloy®, Inconel®, Monel® or fluoropolymers. The reactor may also include means of heat exchange, if necessary.

As used herein, percentages are by molar percent unless specified otherwise.

The following examples illustrate the invention without limiting it.

EXAMPLES

In the following examples, use is made of a catalyst Ni—Cr/AlF$_3$ which is obtained as follows. The catalyst used is a mixed catalyst nickel/chromium of atomic ratio of Ni/Cr=1, supported on alumina fluoride and is prepared by impregnating solutions of nickel and chromic anhydride (CrO$_3$). After impregnation and drying, the solid is treated at a temperature between 320° C. and 390° C. in the presence of a mixture of hydrofluoric acid and nitrogen (concentration by volume of 5 to 10% of this acid in nitrogen). The catalyst bed is placed on a grid welded to the lower end of reactor. The reactor is equipped with a temperature measurement at three locations along the catalyst bed.

Examples 1 to 5

Equilibrium 1234yf/245cb 150 ml of catalyst Ni—Cr/AlF$_3$ are introduced into the reactor. The reaction temperature is 352° C. and atmospheric pressure. The flows of HF and 1233xf are adjusted to obtain a molar ratio HF/1233xf close to 5 but varying contact time: 9.5, 18.8, 26.7, 37.9 and 39 seconds. The products that are mainly obtained are 1234yf and 245cb (if one excludes the 1233xf, not completely converted). The molar compositions 1234yf and 245cb are summarized in table 1. It can be concluded that an equilibrium takes place between 1234yf and 245cb.

|  | Contact time (s) | 1234yf (%) | 245cb (%) |
| --- | --- | --- | --- |
| Ex. 2 | 9.5 | 72.53 | 27.47 |
| Ex. 3 | 18.8 | 69.13 | 30.87 |
| Ex. 4 | 26.7 | 66.49 | 33.51 |
| Ex. 5 | 37.9 | 66.28 | 33.72 |
| Ex. 6 | 39 | 66.18 | 33.82 |

Example 6

Fluorination of 1230xa

It uses a reactor consisting of an Inconel® tube of internal diameter 28 mm and length of 640 mm, placed vertically in a tubular furnace. The catalyst bed consists of a lower layer of 40 mm corundum, and a catalyst layer of 85 mm (volume=50 cm$^3$, mass=42.1 g). The reagents are introduced continuously at the bottom of the reactor and preheated the oven temperature. The gaseous products exit at the upper end of the reactor through a control valve; they are analyzed by gas chromatography.

The operating conditions in the reactor of fluorination are:
Temperature 340° C.;
Absolute pressure 7 bar;
Molar ratio HF/1230xa=40;
Molar ratio O$_2$/(HF+1230xa)=0.135
Contact time=11 sec and 22 sec.

After 200 hours of reaction, the result of analysis of gaseous products (outside hydracids) from the reactor is given in the following table:

|  | Contact time 11 sec | Contact time 22 sec |
| --- | --- | --- |
| Conversion rate of 1230xa | 99.7% | 100.0% |
| Selectivity 1234yf | 0.45% | 2.42% |
| Selectivity 245cb | 0.29% | 2.85% |
| Selectivity 1233xf | 97.7% | 92.7% |
| Selectivity 244bb | 1.1% | 1.1% |
| Selectivity 243db | 0.1% | 0.15% |
| Selectivity «others» | 0.36% | 0.78% |

One will note that the content in 244bb is substantially constant; this compound appears to be an intermediate compound formed during the reaction between 1233xf and 1234yf (further to the reaction 1230xa into 1233xf) on the one hand and during the reaction with 1234yf and 245cb on the other hand. A higher contact time will favour formation of 1234yf, where the equilibrium with 245cb is reached.

The invention claimed is:
1. A composition comprising 2,3,3,3-tetrafluoropropene (1234yf), 1,1,1,2,2-pentafluoropropane (245cb), and 1,1,1,2-tetrafluoro-2-chloropropane (244bb),
wherein:
the molar ratio of 245cb to 244bb ranges from 1:1 to 70:1,
the molar ratio of 1234yf to 245cb ranges from 1:5 to 3:1, and
the 1234yf and the 245cb form an equilibrium;

further wherein said composition is obtainable by a method comprising:
(i) contacting 1,1,2,3-tetrachloropropene (1230xa) with hydrogen fluoride HF in a gas phase in the presence of a fluorination catalyst under conditions effective to produce a reaction mixture comprising 245cb, and
(ii) recycling the 245cb formed to step (i).

2. The composition of claim 1, wherein the molar ratio of 245cb to 244bb ranges from 1.5:1 to 65:1, and the molar ratio of 1234yf to 245cb ranges from 1:4 to 2:1.

3. The composition of claim 1, further comprising 2-chloro-3,3,3-trifluoro-1-propene (1233xf).

4. The composition of claim 3, further comprising hydrofluoric acid (HF).

5. The composition of claim 3, further comprising hydrogen chloride (HCl).

6. The composition of claim 3, further comprising hydrofluoric acid (HF) and hydrogen chloride (HCl).

7. A composition comprising 2,3,3,3-tetrafluoropropene (1234yf), 1,1,1,2,2-pentafluoropropane (245cb), and 1,1,1,2-tetrafluoro-2-chloropropane (244bb), wherein:
the molar ratio of 245cb to 244bb ranges from 1:1 to 70:1,
the molar ratio of 1234yf to 245cb ranges from 1:5 to 3:1, and
the 1234yf and the 245cb form an equilibrium.

* * * * *